United States Patent [19]

Gasc et al.

[11] 4,412,988
[45] Nov. 1, 1983

[54] HEXAPEPTIDES

[75] Inventors: Jean-Claude Gasc, Bondy; Serge Geoffre, Cestas; Michel Hospital, Talence; Jacques Laurent, Issy-les-Moulineaux, all of France

[73] Assignee: Roussel Uclaf, Paris, France

[21] Appl. No.: 310,392

[22] Filed: Oct. 9, 1981

[30] Foreign Application Priority Data

Oct. 14, 1980 [FR] France ............................ 80 21919

[51] Int. Cl.$^3$ .................... C07C 103/52; A61K 37/02
[52] U.S. Cl. ............................. 424/177; 260/112.5 R
[58] Field of Search ................. 424/177; 260/112.5 R

[56] References Cited

FOREIGN PATENT DOCUMENTS 1429195 3/1976 United Kingdom .
1557076 12/1979 United Kingdom .

OTHER PUBLICATIONS

Biochemical Journal, vol. 126, pp. 773–780, 1982.

*Primary Examiner*—Delbert R. Phillips
*Assistant Examiner*—F. T. Moezie
*Attorney, Agent, or Firm*—Hammond & Littell, Weissenberger and Muserlian

[57] ABSTRACT

Novel hexapeptides of the formula

Cys—X—Y—D—Lys—Z     I wherein X is a sequence selected from the group consisting of Ala—Ala and Glu—His, Y is selected from the group consisting of Cys and Phe and Z is Phe when Y is Cys or Z is Cys when Y is Phe, the two Cys groups in the molecule being joined by a disulfide bridge, and their functional derivatives such as their non-toxic, pharmaceutically acceptable acid addition salts, salts with bases, esters and amides and metallic complexes thereof having an influence on the memory process and their preparation.

24 Claims, No Drawings

HEXAPEPTIDES

STATE OF THE ART

French Pat. Nos. 2,358,384 and 2,182,918 and Unlisted Drugs, Vol. 31, No. 11 (Nov. 1979), p. 169 M describe compounds which have an effect on the memory process but their chemical structures are completely different.

OBJECTS OF THE INVENTION

It is an object of the invention to provide the novel compounds of formula I and their functional derivatives and a novel process for their preparation.

It is another object of the invention to provide novel compositions for retarding the extinction of a response to a conditioned retarding avoidance or the disappearance of a taught response or increasing attention, vigilance or memorization and a novel method of inducing such activity in warm-blooded animals.

These and other objects and advantages of the invention will become obvious from the following detailed description.

THE INVENTION

The novel compounds of the invention are hexapeptides of the formula

Cys-X-Y-D-Lys-Z    I wherein X is a sequence selected from the group consisting of Ala-Ala and Glu-His, Y is selected from the group consisting of Cys and Phe, and Z is Phe wherein Y is Cys or Z is Cys wherein Y is Phe the two Cys groups in the molecule being joined by a disulfide bridge, and their functional derivatives such as their non-toxic, pharmaceutically acceptable acid addition salts, salts with bases, esters and amides and metallic complex thereof.

The nomenclature used in the application is IUPAC nomenclature following the rules published in Biochem. J., Vol. 126 (1972), p. 773–780. Conforming to those nomenclature rules, the peptides are designated only by an abbreviation of 3 letters with the L form existing naturally. When the peptides present the D form, the D configuration precedes the 3 letter abbreviation.

The following symbols are used to indicate the following α-amino carboxylic acids: Cys=cysteine; Ala=alanine; Glu=glutamic acid; His=histidine and Phe=phenylalanine.

The functional derivatives of the compounds of formula I include the non-toxic, pharmaceutically acceptable acid addition salts; the salts of non-toxic, pharmaceutically acceptable bases; non-toxic, pharmaceutically acceptable esters and the amides and N-alkyl or N,N-dialkyl amides of 1 to 5 carbon atoms.

Examples of suitable acids for the formation of the acid addition salts are inorganic acids such as hydrochloric acid, hydrobromic acid, nitric acid, sulfuric acid or phosphoric acid and organic acids such as acetic acid, trifluoroacetic acid, formic acid, propionic acid, benzoic acid, maleic acid, fumaric acid, succinic acid, citric acid, tartaric acid, oxalic acid, glyoxylic acid, aspartic acid, alkane sulfonic acids such as methane sulfonic acid or ethane sulfonic acid, aryl sulfonic acids such as benzene sulfonic acid or p-toluene sulfonic acid and arylcarboxylic acids.

Examples of suitable bases to form non-toxic, pharmaceutically acceptable salts are alkali metal carbonates and hydroxides such as sodium hydroxide, sodium carbonate or sodium bicarbonate. Examples of suitable non-toxic, pharmaceutically acceptable esters are alkyl esters of 1 to 5 carbon atoms such as methyl, ethyl and propyl.

Among the preferred compounds of formula I are those wherein X is the sequence Ala-Ala, those wherein X is the sequence Glu-His and their functional derivatives.

Specific preferred compounds of the invention are the cyclic disulfide (1→6) of N-[cysteinylalanylalanyl phenylalanyl-D-lysyl]-cysteine and its acetate, the cyclic disulfide (1→4) of N-[cysteinylalanylalanylcysteinyl-D-lysyl]-phenylalanine and its acetate and the cyclic disulfide (1→4) of N-[cysteinylglutamylhistidylcysteinyl-D-lysyl]-phenylalanine.

Also an object of the invention are the metallic complexes of the compounds of formula I or their functional derivatives and the metallic complexes are formed by classical known methods by contacting the peptides with a metallic salt such as a metallic phosphate or metallic hydroxides or metallic oxides. Examples of suitable metals are cobalt, nickel, copper, iron and preferably zinc. The metal complexes may be prepared from a mixture of the peptide and the metal salt, oxide or hydroxide in an aqueous medium.

The process of the invention for the preparation of the compounds of formula I comprises subjecting α-aminocarboxylic acids with the amino groups blocked to successive condensations in the desired order followed by removal of the protective blocking group and transforming, if desired, the compound of formula I into a functional derivative thereof. To control the reactions, it is necessary to block the amino group of one of the acids and the carboxylic acid group of the other, and the blocking group should be one which is easily removable.

Numerous methods are known for the synthesis of peptides and one of the methods which may be used is described by Merrifield [J.A.C.S., Vol. 85 (1963), p. 2149–2154]. In this method, an amino acid is attached to a solid resin, for example by an ester bond, and the peptide is a result of a plurality of steps to attach successively protected amino acids to develope the peptide chain. The reactants and the byproducts are removed by filtration and when the sequence is assembled in the correct order, the peptide is severed from the solid support.

In the invention, the products of formula I and their functional derivatives are prepared by a series of successive condensation of amino acids using a solid phase support. The amino acids may be attached to any suitable polymer which can simply be easily separated from the reactants and should contain a functional group to which the first protected amino acid may be attached to by a covalent bond. Examples of suitable diverse polymers useful for this are cellulose, polyvinyl alcohol, polymethacrylate and sulfonated polystyrenes as well as a chloromethylene resin of styrene and divinylbenzene which is used in the specific examples.

In a general manner, the functional groups used as protective groups are principally known. The α-amino groups may be protected, for example, by tert.-butoxycarbonyl, carbobenzoxy, adamantyloxycarbonyl or isoborneyloxycarbonyl but the preferred group is tert.-butoxycarbonyl. Trifunctional amino acids may also be protected by their lateral function. For the synthesis of the products of the invention, the amino acids used are Cys, Ala, Glu, His and Dlys. The —SH group of cysteine may be protected by 4-methoxybenzyl, for example and the imidazole group of histidine may be protected by 2,4-dinitrophenyl. The gamma carboxyl group of glutamic acid may be protected by benzyloxy and the ε—NH₂ group of D-lysine may be protected by 2,4-dichloro-benzyloxycarbonyl.

In the synthesis illustrated in the specific examples, the first amino acid is fixed to the resin through the intermediary of a cesium salt as taught by Gisin [Helv. Chem. Acta., Vol. 56 (1973), p. 1476]. The amino acids are coupled with the use of dicyclohexylcarbodiimide and the deblocking of the tert.-butoxy carbonyl group is effected with a 50% hydrofluoric acid in methylene chloride solution. At the end of the synthesis, the 2,4-dinitrophenyl blocking of the imidazole of histidine is removed with mercaptoethanol. The peptide is separated from the resin using hydrofluoric acid which eliminates any other blocking groups of lateral functions.

The compounds of formula I may be changed into their functional derivatives by reacting a compound of formula I with an acid to form the corresponding acid addition salt or by reacting a compound of formula I with a base such as sodium hydroxide, sodium bicarbonate or potassium hydroxide to form the corresponding salt or by reacting a compound of formula I with an alcohol such as methanol, ethanol, propanol, isopropanol or butanol to form the corresponding esters or by forming the amide or mono or dialkyl amides by known methods such as Houben-Weyl, Methoden der Organischen Chemie., 4th Ed., Vol. XVI, p. 315 et al.

The picric acid test giving the titer of free amines may be effected as described by Gisin [Anal. Chim, Acta, Vol. 58 (1972), p. 248] and the amino acid analysis of the peptides produced is effected with a Beckman amino acid analyzer.

The novel compositions of the invention for retarding the extinction of a response to a conditional retarding avoidance or the disappearance of a taught response or increasing attention, vigilance or memorization are comprised of an effective amount of at least one member of the group consisting of a compound of formula I, their functional derivatives and metallic complexes thereof and an inert pharmaceutical carrier or excipient. The compositions may be in the form of tablets, dragees, gelules, granules, suppositories and injectable solutions or suspensions made in the usual fashion.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants or emulsifiers and preservatives.

The compositions are useful for the treatment of intellectual or nervous asthenia, memory failure, major or minor cerebral vascular troubles, senility or intellectual strain.

The preferred compositions of the invention are those wherein X has the sequence Ala-Ala or Glu-His and their functional derivatives and especially those containing as the active ingredient one of the group consisting of the non-toxic, pharmaceutically acceptable acid addition salts; the salts of non-toxic, pharmaceutically acceptable bases; non-toxic, pharmaceutically acceptable esters and the amides and N-alkyl or N,N-dialkyl amides of 1 to 5 carbon atoms.

The novel method of the invention for increasing intellectual capacity of warm-blooded animals, including humans comprises administering to warm-blooded animals an amount of at least one compound of formula I, a functional derivative thereof or a metallic complex thereof sufficient to increase the intellectual capacity. The said compounds may be administered orally, rectally, intranasally, parenterally or sublingually. The usual daily dose is 0,01 μg to 500 mg but will vary depending upon the method of administration and the specific compound. The parenteral daily dose may be 0.01 μg to 500 μg while the usual oral, sublingual and intranasal dose is 0.1 to 500 mg.

Particularly interesting compositions are those containing the peptides of the invention in a form having a prolonged activity such as by transforming the compounds of formula I or a functional derivative thereof into its metallic complex as indicated above.

The examples use for illustration purposes the solid phase technique of Merrifield but other classical techniques for the preparation of peptides may be used to prepare the novel compounds of the invention. For example, the novel products may be prepared by coupling the conveniently protected isolated amino acids or peptides with conveniently protected amino acids or peptides by means of substances activating the carboxylic acid group as described by Houben-Weyl; Methoden der Organischen Chemie., Vol. 15/2, Synthesen von peptides, p. 2–364 (1974) by Georg Thieme Verlag, Stuttgart such as dicyclohexylcarbodiimide, N-ethyl-N'-(dimethylaminopropyl)-carbodiimide, o-nitrophenol, p-nitrophenol or pentachlorophenol with or without the addition of a catalyst.

The following abreviations are used in the examples Boc=Tert.-butoxycarbonyl; 4-MeOBn=4-methoxybenzyl; 2,4-DNP=2,4-dinitrophenyl; OBn=benzyloxy; DCC=dicyclohexylcarbodiimide.

In the following examples there are described several preferred embodiments to illustrate the invention. However, it is to be understood that the invention is not intended to be limited to the specific embodiments.

EXAMPLE 1

Acetate of cyclic disulfide (1→6) of N-[cysteinylalanylalanylphenylalanyl-D-lysyl]-cysteine of the formula:

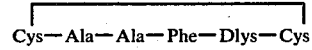

Cys—Ala—Ala—Phe—Dlys—Cys

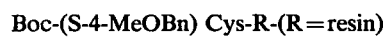

Boc-(S-4-MeOBn) Cys-R-(R=resin)

The fixation of the first amino acid on the resin was effected with 10 g of polystrene with 1% of divinylbenzene-chloromethylene resin with a capacity of 0.87 meq per g of resin in 200 ml of dimethylformamide with the aid of 4.73 g of the cesium salt of Boc S (4-MeOBn) L cysteine prepared by mixing Boc S (4-MeOBn) L cysteine, water, ethanol and cesium carbonate at a pH of 7 at room temperature for one hour. The mixture was stirred at 60° C. for 18 hours and was vacuum filtered. The resin was washed 3 times with 200 ml of dimethylformamide, twice with 200 ml of methanol and 3 times with 200 ml of methylene chloride. The resin was dried under reduced pressure to obtain 13 g of resin titrating 0.4 meq of blocked L cysteine per g of final resin.

Cys-R 13 g of the said resin were treated successively two times with 150 ml of 50% trifluoroacetic acid in methylene chloride over 10 minutes, two times with 150 ml of methylene chloride, once with 150 ml of isopropanol, two times with 150 ml of methylene chloride, two times with 150 ml of 12% of triethylamine in methylene chloride for 10 minutes, two times with 150 ml of methylene chloride once with 150 ml of isopropanol, once with 150 ml of methanol and 6 times with 150 ml of methylene chloride to obtain Cys-R.

$N^\alpha$-Boc-$N^\epsilon$-(2,4-dichlorobenzyloxycarbonyl)-D-lysine-Cys-R

The Cys-R product was added to 15.8 moles of $N^\alpha$-Boc-$N^\epsilon$-(2,4-dichlorobenzyloxycarbonyl)-D-lysine in 150 ml of methylene chloride and then solution of 18 ml DCC in methylene chloride was added thereto. Coupling was determined to be complete after 10 minutes by the negative ninhydrin test and the mixture was washed twice with 150 ml of methylene chloride, once with 150 ml of methanol, once with 150 ml of isopropanol and 5 times with 150 ml of methylene chloride to obtain $N^\alpha$-Boc-$N^\epsilon$-(2,4-dichlorobenzyloxycarbonyl)-D-lysine-Cys-R.

D-Lys-Cys-R

D-Lys-R was deblocked in the same fashion as Cys and the latter was coupled, washed, deblocked with the coupling, washing, deblocking of $\alpha$-amino acids of D-Lys was effected in the following order with the following protected amino acids: Boc L-phenylalanine, Boc L-Alanine, Boc L-Alanine and Boc S (4-methoxybenzyl)-L-Cysteine. After deblocking the last amino acid cysteine), 16.8 g of D-Lys-Cys-R were obtained.

Separation of Peptide from the Resin

In a hydrofluoric acid reactor, there was placed 16.8 g of D-Lys-Cys-R, 18 ml of anisole and 80 ml of condensed hydrofluoric acid and the mixture was stirred at 0° C. for one hour and evaporated to dryness under reduced pressure. The resin was washed three times with ethyl acetate and was extracted successively 4 times with 20 ml of acetic acid and 4 times with 20 ml of water, 4 times with 20 ml of 50% aqueous acetic acid. The combined extracts were lyophilized to obtain 3.9 g of the acetate of Cys-Ala-Ala-Phe-Dlys-Cys. The latter was dissolved in 100 ml of water and the solution was filtered. The filtrate containing Cys-Ala-Ala-Phe-DLys-Cys was immediately used for the cyclization step.

Peptide Cyclization

The said filtrate was added dropwise over 90 minutes to a solution of 4 g of potassium ferricyanide in 500 ml of water while keeping the pH at 7.5 by addition of 1 M ammonium hydroxide solution. The resulting yellow solution was passed through a column of Dowex (Cl$^-$) resin and the resin was washed twice with 300 ml of twice distilled water. The colorless solution was lyophilized to obtain 6 g of raw $$\overline{\text{Cys—Ala—Ala—Phe—D Lys—Cys}}.$$

The said product was purified by high performance liquid chromatography over a silica gel shell carrying $C_{18}$ hydrocarbon chain and successive elutions with first 10 liters of a 15–85 methanol-twice distilled water mixture containing 3 g/l of ammonium acetate and then with 2.5 liters of a 1–4 methanol-twice distilled water mixture containing 3 g/l of ammonium acetate. The last elutate was lyophilized and the product was taken up several times in twice distilled water and lyophilized to a constant weight to obtain 1.91 g of $$\overline{\text{Cys—Ala—Ala—Phe—D Lys—Cys}}$$

with a specific rotation of $[\alpha]_D^{20} = -5°$ (c in water).

| Amino Acid Analysis: | | | | | | | |
|---|---|---|---|---|---|---|---|
| Calculated: | Cys | 2 | Ala | 2 | Phe | 1 | Lys | 1 |
| Found: | | 2.02 | | 2.12 | | 1.02 | | 1 |
| Circular dichroism (water): | | | | | | | |
| Max. at 220 nm | | | | $D_\epsilon = +5.8$ | | | |
| Max. at 270 mn | | | | $D_\epsilon = -0.25$ | | | |

EXAMPLE 2

Acetate of cyclic disulide (1→4) of N-[Cysteinylalanylanylcysteinyl-D-lysyl]-phenylalanine of the formula $$\overline{\text{Cys—Ala—Ala—Cys—D-Lys}}$$

Phe CH$_3$COOH Boc-Phe-R (R=resin)

The fixture of the first amino acid to the resin was effected with 7.5 g of polystyrene resin with 1% divinyl benzene as in Example 1 with the aid of 4.46 g of cesium salt of Boc-Phe-OCs in 95 ml of dimethylformamide and stirring overnight at 55° C. to obtain Boc-Phe-R.

Phe-R

The protective blocking group was removed by reaction with a 50% solution of trifluoracetic acid in methylene chloride for 10 minutes and the amount of Phe in the resin was determined by the picric acid test to be 0.76 meg per g of resin. The resin was then successively washed with dimethylformamide, methylene chloride, isopropanol and then methylene chloride to obtain Phe-R.

Boc-D-Lys-Phe-R

The coupling of Phe-R was effected with 4.49 g of N$\alpha$-Boc-N$\epsilon$-(2,4-dichlorobenzyloxycarbonyl)-D-Lys with 13 ml of a 1 M solution of DCC in methylene chloride. The coupling reaction was determined to be complete in one hour by the negative ninhydrin test and the product was washed successively with 150 ml of methylene chloride, 150 ml of methanol, 150 ml of isopropanol and 5 times with 150 ml of methylene chloride to obtain Boc-D-Lys-R. The Boc protective group was removed by reacting the product for 10 minutes with a 50% trifluoroacetic acid in methylene chloride solution. The product was washed with dimethylformamide, methylene chloride and methanol to obtain Boc D-Lys-Phe-R.

Boc-(S-4-methoxy-Bn)-Cys-D Lys-Phe-R

The above product was coupled with 3.41 g of Boc-(S-4-methoxy-Bn)-Cys in 13 ml of a solution of 1 M DCC in methylene chloride and the coupling was determined to be complete after one hour by a negative ninhydrin test. The mixture was stirred for 20 hours and the product was washed to obtain Boc-(S-4-methoxy-Bn)-Cys-D Lys-Phe-R. The Boc blocking group was removed with trifluoroacetic acid and was washed as un the above couplings to obtain Boc-(S-4-methoxy-Bn)-Cys-D Lys-Phe-R.

Cys-Ala-Ala-Cys-D-Lys-Phe-R

The latter product was subjected to successive couplings, washings, deblocking and washing as previously with the following protected amino acids: Boc-Ala, then Boc-Ala and finally Boc-(S-4MeOBn)-Cys to obtain 14.5 g of Cys-Ala-Ala-Cys-D Lys-Phe-R.

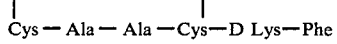

14.5 g of the latter resin, 14.5 ml of anisole and sufficient condensed hydrofluoric acid at −80° C. under reduced pressure for a total volume of 100 ml were placed in a hydrofluoric acid reactor and the mixture was stirred at 0° C. for 45 minutes and evaporated to dryness under reduced pressure. The resin was washed with ethyl acetate and was then extracted by alternate washings with distilled water and acetic acid. The extracts were filtered and the filtrate was lyophilized to obtain 4.2 g of Cys-Ala-Ala-Cys-D Lys-Phe acetate.

The latter product in 350 ml of water was stirred and was then filtered and the filtrate was poured into 450 ml of a 0.02 M solution of potassium ferricyanide while keeping the pH between 6.5 and 7 with 1 M ammonia. The pH is then brought to 5 by addition of acetic acid. The solution was stirred with Dowex (Cl⁻) resin and the mixture was filtered. The filtrate was evaporated to dryness under reduced pressure at 25° C. and the residue was taken up in water. The solution was lyophilized to obtain 6 g of the acetate of

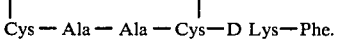

The said raw product was purified by high performance liquid chromatograpy with a Prep 500 WATERS apparatus provided with a silica gel- $C_{18}$ shell and the product was eluted with first a 1-3 methanol-water mixture containing 3 g/l of ammonium acetate, then a 21-79 methanol-water mixture containing 3 g/l of ammonium acetate, then a 22-78 methanol-water mixture contain 3 g/l of ammonium acetate and finally a 23-77 methanol-water mixture containing 3 g/l of ammonium acetate to obtain 0.365 g of

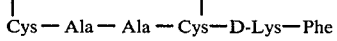

with a specific rotation of $[\alpha]_D^{20} = +16°$ (c=0.5% in water).

| Amino Acid Analysis: | | | | | | | |
|---|---|---|---|---|---|---|---|
| Calculated: | Cys | 2 | Ala | 2 | Cys | 1 | Phe | 1 |
| Found: | | 1.96 | | 2.06 | | 1.08 | | 1 |
| Circular dichroism (water): | | | | | | | |
| Max. at 211 nm | | | | $D_\epsilon = +4.7$ | | | |
| Max. at 229 nm | | | | $D_\epsilon = -6.0$ | | | |
| Max. at 285 nm | | | | $D_\epsilon = +0.3$ | | | |

EXAMPLE 3

Cyclic disulfide (1→4) of N-[cysteinylglutamylhistidylcysteinyl-D-lysyl]-phenylalanine of the formula

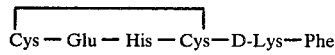

Boc-Phe-R (R=resin)

Phe was reacted by the procedure of Example 1 with 5 g of a polystrene resin with 1% of divinylbenzene chloromethylene with the help of 2.978 g of Boc-Phe-OCs dissolved in 50 ml of dimethylformamide. The mixture was stirred at 50° C. for 20 hours to obtain Boc-Phe-R which was deblocked as in Example 1.

Cys-Glu-(2,4-DNP)-His-Cys-D-Lys-Phe-R

Phe-R was subjected to successive couplings using the procedure of Example 1 with the following protected amino acids: $N^\alpha$-Boc-$N^\epsilon$-(2,4-dichloro-benzyloxycarbonyl)-D Lys, Boc-(S-4-MeOBn)-Cys and α-Boc-(2,4-DNP)-His, then, the α-Boc group was removed by treatment with 50% trifluoroacetic acid in methylene chloride and then 2,4-dinitrophenyl was eliminated with 2-mercapto-ethanol to obtain 10 g of Cys-Glu-(2,4-DNP)-His-Cys-D Lys-Phe-R.

Cys-Glu-His-Cys-D-Lys-Phe-R

The 10 g of the latter compound were added to a mixture of 100 ml of dimethylformamide and 100 ml of 2-mercaptoethanol and the pH of the mixture was adjusted to 8 by addition of triethylamine. The mixture was stirred for 18 hours at room temperature and was vacuum filtered. The product was washed successively with dimethylformamide, ethyl acetate, methylene chloride, methanol and methylene chloride and was dried under reduced pressure to obtain 9.75 g of Cys-Glu-His-Cys-D Lys-Phe-R.

Cys-Glu-His-Cys-D-Lys-Phe-acetate

A mixture of 4.875 g of the latter product, 5 ml of anisole and 50 ml of redistilled hydrofluoric acid was stirred at 0° to 5° C. for 45 minutes and was then evaporated to dryness under reduced pressure. The resin was washed with ethyl acetate and was then extracted with acetic acid and then with water. The extracts were filtered and the filtrate was lyophilized to obtain 2.143 g of Cys-Glu-His-Cys-D Lys-Phe-acetate.

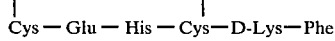

The latter product was cyclized as in Example 2 to obtain 1.704 g of raw product which was purified with carboxymethylcellulose. The raw product was dissolved in a solution of aqueous 0.025 M ammonium acetate with a pH of 4 and the solution was passed through a column. Elution was with first a 0.025 M solution of ammonium acetate and then with a 0.05 M solution of ammonium acetate and the solution was lyophilized to obtain 422 mg of

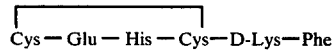

Cys — Glu — His — Cys—D-Lys—Phe with a specific rotation of $[\alpha]_D^{20} = +11° \pm 2°$ (c=0.5% in water).

| | Amino acid Analysis: | | | | |
|---|---|---|---|---|---|
| Calculated: | Cys 2 | Glu 1 | His 1 | D Lys 1 | Phe 1 |
| Found: | 1.6 | 1 | 1.02 | 1.12 | 1.12 |
| | Circular dichroism (water): | | | | |
| | Max. ≅ 222 nm | | | $D_\epsilon \cong -2.8$ | |
| | Max. ≅ 260 nm | | | $D_\epsilon \cong -0.2$ | |

PHARMACOLOGICAL DATA

The action against extinction of a practice of active avoiding a negative reinforcement was determined using an apparatus described by deWeid (Proc. Soc. Ex. Biol. Med.,) Vol. 122 (1466) p. 28). The practice is effected in a box equipped with a 60 W lamp (conditional stimulus: CS), a mat and an electrifiable floor connected to an electric stimulus which permits the delivery of a painful shock of 75 volts (unconditional stimulus US). The conditional stimulus is present only for 5 seconds, then is associated with an unconditional stimulus just as the animal grips the mat realizing as well the avoidance response desired. The conditional response is acquired when the animal responds to the conditional stimulus.

10 tests at 60 second intervals were effected daily for 3 days and examination of the extinction of the practice realized with suppression of the unconditional stimulus is followed on the 4th day with 3 tests at 2 hour intervals with the animals presenting at least 7 conditional responses.

The compounds were injected subcutaneously as a phosphate-zinc complex before the first test of extinction of practice to group of 5 rats and the results were compared with an untreated control group of rats. The evolution of the conditional response in the course of the period of extinction of practice 2 and 4 hours after the injection of the compound is expressed as the percent of variation with respect to the number of conditional responses observed in the first test of extinction before treatment. The results are reported in Table I.

TABLE I

| Product of Example | Dose in µg/rat | % of conditional response in course of extinction period | |
|---|---|---|---|
| | | after 2 hours | after 4 hours |
| None | | 60 | 30 |
| 1 | 1 | 51 | 49 |
| | 10 | 76 | 71 |
| 2 | 1 | 59 | 35 |
| | 10 | 71 | 75 |
| 3 | 1 | 75 | 29 |
| | 10 | 70 | 50 |

The results of Table I show that the products of the invention retarded the extinction of the practice which appeared in the course of time in the absence of reenforcement. The reenforcement which is a negative reenforcement is constituted by an unconditional stimulus.

Various modifications of the products and process of the invention may be made without departing from the spirit or scope thereof and it is to be understood that the invention is intended to be limited only as defined in the appended claims.

What we claim is:

1. A compound selected from the group consisting of hexapeptides of the formula

Cys-X-Y-D-Lys-Z          I wherein x is a sequence selected from the group consisting of Ala-Ala and Glu-His, Y is selected from the Group consisting of Cys and Phe, Z is Phe when Y is Cys or Z is Cys when Y is Phe, the two Cys groups in the molecule being joined by a disulfide bridge, their non-toxic, pharmaceutically acceptable acid addition salts; their salts of non-toxic, pharmaceutically acceptable bases, their non-toxic, pharmaceutically acceptable esters and their amides and N-alkyl or N,N-dialkyl amides of 1 to 5 carbon atoms and their metallic complexes with a metal selected from the group consisting of cobalt, nickel, copper, iron and zinc.

2. A compound of claim 1 wherein X is the sequence Ala-Ala.

3. A compound of claim 1 wherein X is the sequence Glu-His.

4. A compound of claim 1 which is selected from the group consisting of the cyclic disulfide (1→6) of N-(cysteinylalanylalanylphenylalanyl-D-lysyl)-cysteine and its acetate.

5. A compound of claim 1 which is selected from the group consisting of the cyclic disulfide (1→4) of N-(cysteinylalanylalanylcysteinyl-D-lysyl)-phenylalanine and its acetate.

6. A compound of claim 1 which is the cyclic disulfide (1→4) of (N-cysteinylglutamylhistidinylcysteinyl-D-lysyl)-phenylalanine.

7. A complex metallic derivative of claim 1 wherein the metal is selected from the group consisting of cobalt, nickel, copper, iron and zinc.

8. The complex of claim 7 wherein the metal is zinc.

9. A composition for retarding the extinction of a response to a conditional retarding avoidance or the disappearance of a taught response or increasing attention, vigilance or memorization comprising an amount of at least one compound of claim 1 sufficient to obtain said effect and a pharmaceutical carrier.

10. The composition of claim 9 wherein X is the sequence Ala-Ala.

11. The composition of claim 9 wherein X is sequence Glu-His.

12. The composition of claim 9 which is selected from the group consisting of the cyclic disulfide (1→6) of N-(cysteinylalanylalanylphenylalanyl-D-lysyl)-cysteine and its acetate.

13. The composition of claim 9 which is selected from the group consisting of cyclic disulfide (1→4) of N-(cysteinylalanylalanylcysteinyl-D-lysyl)-phenylalanine and its acetate.

14. The composition of claim 9 which is the cyclic disulfide (1→4) of (N-cysteinylglutamylhistidinylcysteinyl-D-lysyl)-phenylalanine.

15. A composition of claim 10 which is a metallic complex wherein the metal is selected from the group consisting of cobalt, nickel, copper, iron and zinc.

16. The composition of claim 9 wherein the metal is zinc.

17. A method for retarding the extinction of a response to a conditional retarding avoidance or the disappearance of a taught response or increasing attention, vigilance or memorization of warm-blooded animals comprising administering to warm-blooded animals an amount of at least one compound of claim 1 sufficient to obtain said effect.

18. The method of claim 17 wherein X is the sequence Ala-Ala.

19. The method of claim 17 wherein X is the sequence Glu-His.

20. The method of claim 17 wherein the compound is selected from the group consisting of the cyclic disulfide (1→6) of N-(cysteinylalanylalanylphenylalanyl-D-lysyl)-cysteine and its acetate.

21. The method of claim 17 wherein the compound is selected from the group consisting of cyclic disulfide (1→4) of N-(cysteinylalanylalanylcysteinyl-D-lysyl)-phenylalanine and its acetate.

22. The method of claim 17 wherein the compound is selected from the group consisting of the cyclic disulfide (1→4) of (N-cysteinylglutamyhistidinylcysteinyl-D-lysyl)-phenylalanine.

23. The method of claim 17 wherein the compound is a complex metallic derivative wherein the metal is selected from the group consisting of cobalt, nickel, copper, iron and zinc.

24. The method of claim 23 wherein the metal is zinc.

* * * * *